United States Patent
Rowe et al.

(10) Patent No.: US 9,241,902 B2
(45) Date of Patent: Jan. 26, 2016

(54) CHEWABLE SOFT CAPSULES CONTAINING UNGELATINIZED STARCH

(75) Inventors: Dennis Rowe, Swindon (GB); Kelvin Royce Garnett, Swindon (GB)

(73) Assignee: R.P. Scherer Technologies, LLC, Las Vegas, NV (US)

(*) Notice: Subject to any disclaimer, the term of this patent is extended or adjusted under 35 U.S.C. 154(b) by 610 days.

(21) Appl. No.: 10/739,451

(22) Filed: Dec. 17, 2003

(65) Prior Publication Data

US 2005/0136104 A1 Jun. 23, 2005

(51) Int. Cl.
| A61K 9/66 | (2006.01) |
| A61K 9/68 | (2006.01) |
| A61K 9/64 | (2006.01) |
| A61K 9/00 | (2006.01) |
| A61K 9/48 | (2006.01) |

(52) U.S. Cl.
CPC ............ *A61K 9/0056* (2013.01); *A61K 9/4816* (2013.01)

(58) Field of Classification Search
CPC ............ A61K 9/48; A61K 9/64; A61K 9/66; A61K 9/68
USPC ......... 424/441, 451, 452, 455, 456, 439, 484, 424/488, 35, 37, 48, 49, 360, 361, 401, 424/489; 514/774, 777–778; 426/549, 576, 426/578–579, 654; 427/3, 214, 220, 221; 106/126, 130
See application file for complete search history.

(56) References Cited

U.S. PATENT DOCUMENTS

| 3,851,051 | A | | 11/1974 | Misket et al. ................. 424/37 |
| 3,865,603 | A | * | 2/1975 | Szymanski et al. ........ 106/145.1 |
| 4,026,986 | A | * | 5/1977 | Christen et al. ............... 264/301 |
| 4,362,755 | A | * | 12/1982 | Mitchell et al. ............... 426/579 |
| 4,532,126 | A | | 7/1985 | Ebert et al. ...................... 424/48 |
| 4,804,542 | A | | 2/1989 | Fischer et al. |
| 4,816,259 | A | * | 3/1989 | Matthews et al. ............. 424/463 |
| 4,935,243 | A | * | 6/1990 | Borkan et al. ................. 424/441 |
| 5,294,249 | A | | 3/1994 | Luisi et al. |
| 5,554,385 | A | * | 9/1996 | Stroud ........................... 424/452 |
| 5,688,521 | A | | 11/1997 | Bolder et al. |
| 5,711,975 | A | * | 1/1998 | Gonze et al. ...................... 426/3 |
| 5,817,323 | A | * | 10/1998 | Hutchinson et al. .......... 424/439 |
| 6,110,486 | A | | 8/2000 | Dugger, III .................... 424/435 |
| 6,258,380 | B1 | | 7/2001 | Overholt |
| 6,258,381 | B1 | | 7/2001 | Luber et al. |
| 6,280,767 | B1 | * | 8/2001 | Sano et al. ..................... 424/456 |
| 6,340,473 | B1 | * | 1/2002 | Tanner et al. ................. 424/451 |
| 6,387,400 | B1 | * | 5/2002 | Tindal et al. .................. 424/455 |
| 7,118,764 | B2 | * | 10/2006 | Carbone et al. ............... 424/489 |
| 2003/0215495 | A1 | * | 11/2003 | Lin et al. ........................ 424/452 |
| 2003/0232076 | A1 | * | 12/2003 | Makino et al. ................. 424/456 |
| 2004/0087669 | A1 | | 5/2004 | Hausmanns et al. |
| 2005/0070703 | A1 | | 3/2005 | Muller et al. |
| 2005/0163833 | A1 | | 7/2005 | Muller |

FOREIGN PATENT DOCUMENTS

| EP | 0284569 | | 9/1988 |
| EP | 0374359 | | 6/1990 |
| EP | 1 447 082 | A1 | 8/2004 |
| JP | 63-500597 | | 3/1988 |
| JP | 8-511795 | | 12/1996 |
| JP | 2003-55198 | A | 2/2003 |
| JP | 2003-199809 | A | 7/2003 |
| JP | 2003-221323 | A | 8/2003 |
| JP | 2003-299714 | A | 10/2003 |
| JP | 2004-513144 | A | 4/2004 |
| JP | 2004-526664 | A | 9/2004 |
| JP | 2005-508359 | A | 3/2005 |
| WO | 95/00123 | | 1/1995 |
| WO | 00/51574 | | 9/2000 |
| WO | 00/61117 | | 10/2000 |
| WO | 02/17855 | A2 | 3/2002 |
| WO | 03/035044 | A2 | 5/2003 |
| WO | 03/043609 | A1 | 5/2003 |
| WO | WO03/090726 | A2 * | 11/2003 |

OTHER PUBLICATIONS

Gennaro, A.R., Ed., Remington's Pharmaceutical Science, 18th Edition, Mack Publishing Co., Easton, PA, 1539-1540 (1990).
Gennaro, A.R., Ed., Remington's Pharmaceutical Science, 17th Edition, Mack Publishing Co., Easton, PA, 1629-1631 (1985).
Patel et al., "Advances in Softgel Formulation Technology," Manufacturing Chemist, 60(7), 26-28 (1989).
Shah et al., "Elasticity of Soft Gelatin Capsules Containing Polyethylene Glycol 400-Quantitation and Resolution," Pharmaceutical Technology, Mar. 1992, 126-130 (1992).
Patel et al., "Factors Affecting the Chemical Stability of Carboxylic Acid Drugs in Enhanced Solubility Systems (ESS) Softgel Formulations based on Polyethylene Glycol (PEG)," Drug Development and Industrial Pharmacy, 18(1), 1-19 (1992).
Patel et al., "Softgel Technology," Manufacturing Chemist, 60(8), 47-49 (1989).

* cited by examiner

*Primary Examiner* — Michael G Hartley
*Assistant Examiner* — Jagadishwar Samala
(74) *Attorney, Agent, or Firm* — Fitzpatrick, Cella, Harper & Scinto

(57) ABSTRACT

A soft chewable capsule film suitable for medicament or foodstuff encapsulation, and a method of fabricating capsules from such a film. Such capsules demonstrate fast rupture in the oral cavity, good mouth feel and chewability, and rapid dissolution of the shell components. In particular, the modified starch is substantially ungelatinized, due at least in part to the processing temperature, and may act as a water retention agent to promote hydration. Additionally, gelatins are selected for bloom strengths that result in a robust capsules that may be fabricated at a thinner wall thickness than previously experienced in the art. Accordingly, such thin capsules have a smaller mass than traditional capsules of the same size and dissolve more quickly than chewable capsules having greater thicknesses. The capsules may be fabricated by a rotary die process at speeds greater than those generally known for soft chewable capsules.

14 Claims, 2 Drawing Sheets

**Light micrographs by polarised light
showing Maltese crosses of ungelatinised grains**

Bar = 100μ ⎯⎯  Bar = 20μ ⎯⎯

Plate 1a Sample TBO097

Plate 1b Sample TBO097

Plate 2a Sample TBO091

Plate 2b Sample TOB091

Plate 3a Sample TBO089

Plate 3b Sample TBO089

FIG. 1

Light micrographs of samples stained in iodine in potassium iodide showing starch black and gelatin yellow

Bar = 100μ ——    Bar = 20μ ——

Plate 4a Sample TB097

Plate 4b Sample TB097

Plate 5a Sample TB091

Plate 5b Sample TB091

Plate 6a Sample TB089

Plate 6b Sample TB089

FIG. 2

CHEWABLE SOFT CAPSULES CONTAINING UNGELATINIZED STARCH

TECHNICAL FIELD

The instant invention relates to a soft gelatin capsule containing a substantial quantity of ungelatinized starch and a method for the formulation thereof, in particular, to a composition and method of manufacturing that produces soft gelatin capsules have both structure and stability sufficient for commercial production, including production as an edible soft chewable capsule.

BACKGROUND OF THE INVENTION

Common routes for the administration of pharmacologically active agents are a plurality of oral dosage forms, including such familiar forms as tablets, pills, and capsules. Such dosage forms are generally fairly convenient, stable in storage and transport, and familiar to the user. However, they are not without problems, and these problems are often significant. It is extremely difficult for most people to swallow any of these oral dosage forms without supplemental water. In the fast-paced world, it is frequently inconvenient or messy to have to take supplementary water with oral medicaments. Such difficulties are compounded for those with difficulty in swallowing, such as, for example, children and the elderly. Certain medical conditions, such as Parkinsonism or other neurological states, make it difficult to swallow oral dosage forms, even with supplemental water.

Additionally, swallowing oral dosage forms intact implicates a complex system of variables involved in gastrointestinal dissolution of dosage forms and absorption of drugs.

Accordingly, there is considerable interest in oral medicaments and so-called pre-gastric absorption of the active ingredient, that is, absorption of the active ingredient from that part of the alimentary canal prior to the stomach. The term "pre-gastric absorption" thus includes buccal, sublingual, oropharyngeal and esophageal absorption. Medicaments absorbed by such pre-gastric absorption pass straight into the systemic circulatory system thereby avoiding first pass metabolism in the liver. Accordingly, bioavailability of agents absorbed in this way may also be increased. This means that the dose of such agents may be reduced while still producing the desired beneficial effects and this decrease in dose may result in a corresponding reduction of unwanted side effects. Current research, as noted in U.S. Pat. No. 6,110,486 to Dugger, shows in particular that absorption through the buccal mucosa represents an often underappreciated route of oral administration that is unavailable to drugs in tablet, pill, or capsule form. There are also non-oral mucosal absorption sites, such as rectal or vaginal mucosa, that may serve as administration routes for dissolvable medications.

Additionally, a wide range of foodstuffs and oral hygiene products, such as breath fresheners, are obviously orally dispensed. Compositions comprising gelatin are widely used to carry such materials. Gelatin, which is normally utilized in such formulations, is defined as a protein obtained by partial hydrolysis of animal collagenous tissues, such as skins, tendons, ligaments and bones; or various collagenous portions of warm and cold water fish. Thin gelatin strips have been employed, particularly for dispensing breath freshening agents, but these are limited in the amount of active ingredient that can be carried by the thin strips. Much research has been devoted to gelatin capsules that may be broken up in the mouth, and at least partially dissolved by chewing. Gelatin capsules of varying compositions are widely known in the art, but in general, are compounded of various mixtures of gelatin, a plasticizer or plasticizers, and water.

A tension has always existed in the formulation of gelatin capsules, namely, that dosing, stability, and storage and handling characteristics are generally furthered by relatively high gelatin content and a relatively low plasticizer and end water content in the capsules as dispensed; while chewability, mouth feel, and therefore, client acceptance, are generally furthered by lower gelatin content and higher plasticizer and end water contents. With capsules designed to be swallowed intact, generally denominated "hard" gelatin capsules, or soft gel capsules designed to be broken in the mouth and then swallowed, this tension is relatively minor. However, with capsules designed to be broken up in the mouth and completely or nearly completely dissolved by chewing, that is, the so-called "chewable soft" gelatin capsule, this tension is difficult to resolve. Such true "chewable soft" capsules are a type of soft gelatin capsule that is particularly distinguished by both a pleasant chewing experience and a complete or near complete dissolution in a short period of time in the oral cavity. Such capsules are also distinguished by particular fabrication problems, such as excessive stickiness during rotary die encapsulation and sticking of the product to other capsules during post-encapsulation handling. Gelatin capsules with high end water content typically have poor storage performance, sticking to one another in bulk packaging and often melting or leaking during storage.

U.S. Pat. No. 4,935,243 to Borkan, et al. discloses a chewable gelatin capsule composition that comprises less than about 30%, and preferably comprises about 20-26% water, and is directed to the use of a hydrogenated starch hydrolysate, which allowed a lower than expected end water content. U.S. Pat. No. 4,532,126 to Ebert, et al. discloses examples of soft gelatin capsules formed at as high as 37% water content, but specifies that these capsules were then subsequently dried to some undisclosed final end water content, in order to obtain desired chewing characteristics.

U.S. Pat. No. 3,851,051 to Miskel et al. discloses numerous embodiments of a soft gelatin capsule that has an initial capsule shell water content of between 28.3 and 36.6%, but further discloses that the capsules are then dried to be in equilibrium with the internal gel-lattice composition, which has a water content of 15-20%. In U.S. Pat. No. 6,258,380 to Overholt, capsules are fabricated from a wet mass that is initially as much as 30% water by weight, but is then subsequently dried to 6%-8% water.

In addition to the effects of water content, chewability of capsules can be affected by the bloom strength and the melting points of the gelatin used in the encapsulation process. In general, gelatins of lower bloom strength and lower melting point have preferable organoleptic qualities, Co-owned U.S. Utility patent application Ser. No. 10/456,450 to Makino; accomplished a high degree of hydration using fish gelatin having a low sol-gel transition temperature, that is, a relatively low melting point. However, such formulations can be problematic when stored at high temperatures or high humidity. For example, it is very difficult to formulate a fish gelatin capsule that will be stable at a storage temperature above 35° C. Capsules made with such low melting point gelatins tend to become sticky during storage, and may even burst or melt, releasing their contents. On the other hand, it is known that mammalian gelatins, some of which have melting temperatures above 60° C., tend to be much more stable at higher storage temperatures, but to often have poorer organoleptic qualities. The research behind the instant invention was designed to pursue the goal of increasing heat stability, at least in part by exploring gelatins of higher bloom strength and mammalian origins, while maintaining the excellent organoleptics seen in fish gelatins with low bloom strengths, low melting points, and/or high water contents.

In sum, the art has needed a material and method for the formulation of commercially acceptable chewable gelatin capsules having organoleptic properties similar to those seen with high end water content capsules, that is, capsules having a high water content at the time the capsules are packaged and made available for sale. This is to be accomplished by manipulation of the gelatin, plasticizer, and starch components, while maintaining water levels in the capsules that are within the normal range for such formulations. Additionally, these capsules, which do not have excessively high water contents, should exhibit stability under reasonably expected storage times and conditions.

SUMMARY OF THE INVENTION

In its most general configuration, the present invention advances the state of the art with a variety of new capabilities and overcomes many of the shortcomings of prior materials and methods in new and novel ways. In its most general sense, the present invention overcomes the shortcomings and limitations of the prior art in any of a number of generally effective compositions and methods. The instant invention demonstrates such capabilities and overcomes many of the shortcomings of prior compositions and methods in new and novel ways.

The instant invention provides for a high water content, chewable soft gelatin capsule with improved organoleptic properties, that is, improved sensory impressions to the user. The capsule and method of formulation thereof accomplishes this by a multifactorial approach involving, among other things, manipulation of the origin, bloom strengths, and melting points of gelatin and mixtures of gelatin; the use of substantially ungelatinized starch as a water retention agent; the fabrication of thinner than expected gelatin films for use in the encapsulation process; only partial drying to a high end water content; and dusting of the capsules with an anti-stickiness, and possibly active, surface treatment agent. As is detailed below, such surface agents may include a plurality of dry agents, such as starches, or may include various waxes, liquid, and polyol applications. The surface treatment agents may be inert, designed solely to combat stickiness, may act to enhance, complement, or ameliorate some aspect of the capsule fill, or may simply act as a desirable flavoring agent for the capsule. This multifactorial approach and illustrative examples are detailed below.

There is disclosed an edible, chewable, soft gelatin capsule comprising a capsule shell formed from a capsule film, the capsule film having a wet mass comprising gelatin in about 29 weight %; hydroxypropylated starch in about 11 weight %; glycerol in about 33 weight/w %; and water in about 27 weight %.

There is further disclosed a finished gelatin capsule ready for packaging, comprising a capsule shell formed from a capsule film; wherein the finished capsule shell has an end composition comprising at least one gelatin in about 20 to 55 weight % gelatin; plasticizer in about 19-40 weight %; and at least one modified starch in about 5-35 weight %.

In addition, there is disclosed a process for making an edible compound for forming capsules comprising the steps of selecting a base gelatin for the edible compound; placing the base gelatin in a temperature controlled mixing unit; adding a predetermined amount of purified water to the mixing unit to create a gel mass; maintaining the gel mass at a temperature no greater than 65° C.; mixing predetermined amounts of at least one predetermined starch and a predetermined amount of at least one plasticizer in a separate vessel to create a slurry; transferring the slurry to the gel mass to create an encapsulation formulation; maintaining the formulation at temperature less than about 65° C.; applying vacuum to deaerate the formulation; transferring the formulation to a temperature controlled vessel and maintaining the temperature thereof at less than about 65° C.; and transferring the formulation to a rotary die encapsulation machine for processing.

There is further disclosed a rotary die gelatin encapsulation process comprising the steps of casting at a first predetermined speed a continuous first gelatin ribbon having a first predetermined thickness on a first casting drum having a first predetermined temperature cooled to less than ambient temperature; casting at a second predetermined speed a continuous second gelatin ribbon having a second predetermined thickness on a second casting drum having a second predetermined temperature cooled to less than ambient temperature; uniting the first gelatin ribbon and the second gelatin ribbon to form gel pockets and injecting fill material into the gel pockets to produce freshly formed gelatin capsules; and processing the freshly formed capsules to reduce surface tackiness.

The plasticizers useful in the present invention are those well known in the prior art and include sorbitol, glycerin, mannitol, polyethylene glycol and the like.

In a more preferred embodiment, the gelatin comprises 20-40 weight %, more preferably 7-30 weight % of the capsule. In a further embodiment of the invention, the gelatin may be bovine gelatin or a mixture of fish and bovine gelatins or a combination of a plurality of fish gelatins.

The dusting agent useful in the present invention may be any confectionary or starch material known to the candy industry to prevent capsules sticking together. The dusting agent may be a starch and is most preferably tapioca starch.

DETAILED DESCRIPTION OF THE INVENTION

The high water content chewable gelatin capsules of the instant invention enables a significant advance in the state of the art. The preferred embodiments of the apparatus accomplish this by new and novel combinations of elements which demonstrate previously unavailable but preferred and desirable capabilities.

The detailed description set forth below is intended merely as a description of the presently preferred embodiments of the invention, and is not intended to represent the only form in which the present invention may be constructed or utilized. The description sets forth the designs, functions, means, and methods of implementing the invention in connection with the enumerated embodiments. It is to be understood, however, that the same or equivalent functions and features may be accomplished by different embodiments that are also intended to be encompassed within the spirit and scope of the invention.

As discussed, an important method of improving organoleptics in the fabrication of chewable soft capsules has been the maintenance of as high a proportion of water as is feasible in the finished product. This goal has proven hard to achieve. As gelatin capsules increase in water content, they become increasingly fragile, sticky, and unstable. Accordingly, the instant invention has combined a multifactorial approach in modifying both the material of the capsule and the fabrication method of the encapsulation process in order to maximize the organoleptic properties of the capsules and the stability thereof.

Modifications of Capsule Formulations

Origin, Bloom Strength and Melting Point of Gelatins

It is found that gelatin capsules of differing characteristics may be fabricated, by varying levels of other materials in the compositions; such as plasticizers, starches, and water, with gelatin contents between at least 20 and 55 weight %. For example, plasticizers may be utilized at least in contents from 19-40 weight %, and starches from at least 5-35 weight %. However, gelatin, being a naturally derived biological agent, is not uniform and it is also found that factors such as origin, bloom strength, and melting point of gelatin greatly affect a capsule, formed of gelatin, in its organoleptic and performance characteristics. Accordingly, along with other variations in the basic capsule film formulation detailed below, experimentation was undertaken with fish gelatins of differing bloom strengths, and hence, inherently higher melting temperatures; mammalian gelatins; and combinations of fish gelatin and mammalian gelatin, with the goal of formulating an improved gelatin capsule that maintained the organoleptic properties of these fish gelatin capsules.

Use of Substantially Ungelatinized Starch as a Water Retention Agent

U.S. Pat. No. 6,340,473 ('473) to Tanner et al. teaches the use of modified starch as an adjunct with carrageenan in the manufacture of soft gelatin capsules. In a ratio of at least 1.5:1, and preferably in a preferred range of 1.5:1 to 4:1 with carrageenan, modified starch was found to interact with carrageenan to produce films that may be reversibly stretched during a capsule filling step, and additionally, can be formed into films that have sufficient structure, elasticity and strength to be removed from a temperature controlled casting surface. As starches are well known in the art to be capable of acting as water retention agents, experimentation was undertaken utilizing a relatively small amount of modified starch as an adjunct to improve the plasticity and organoleptic properties of various gelatin combinations. At all times during processing, the melt, capsule film and capsules are kept below 65° C., the gelation temperature of modified starch, so that the starch acts as a water retention agent, and not as a matrix forming agent. At the process temperature of the instant invention of below 65° C., a substantial amount of the starch will remain in granular form. Such granular starch may additionally act as a disintegrants; since non-gelatinized starch is capable of swelling during hydration, this swelling can act to increase the break-up of a capsule film.

Figure 1:
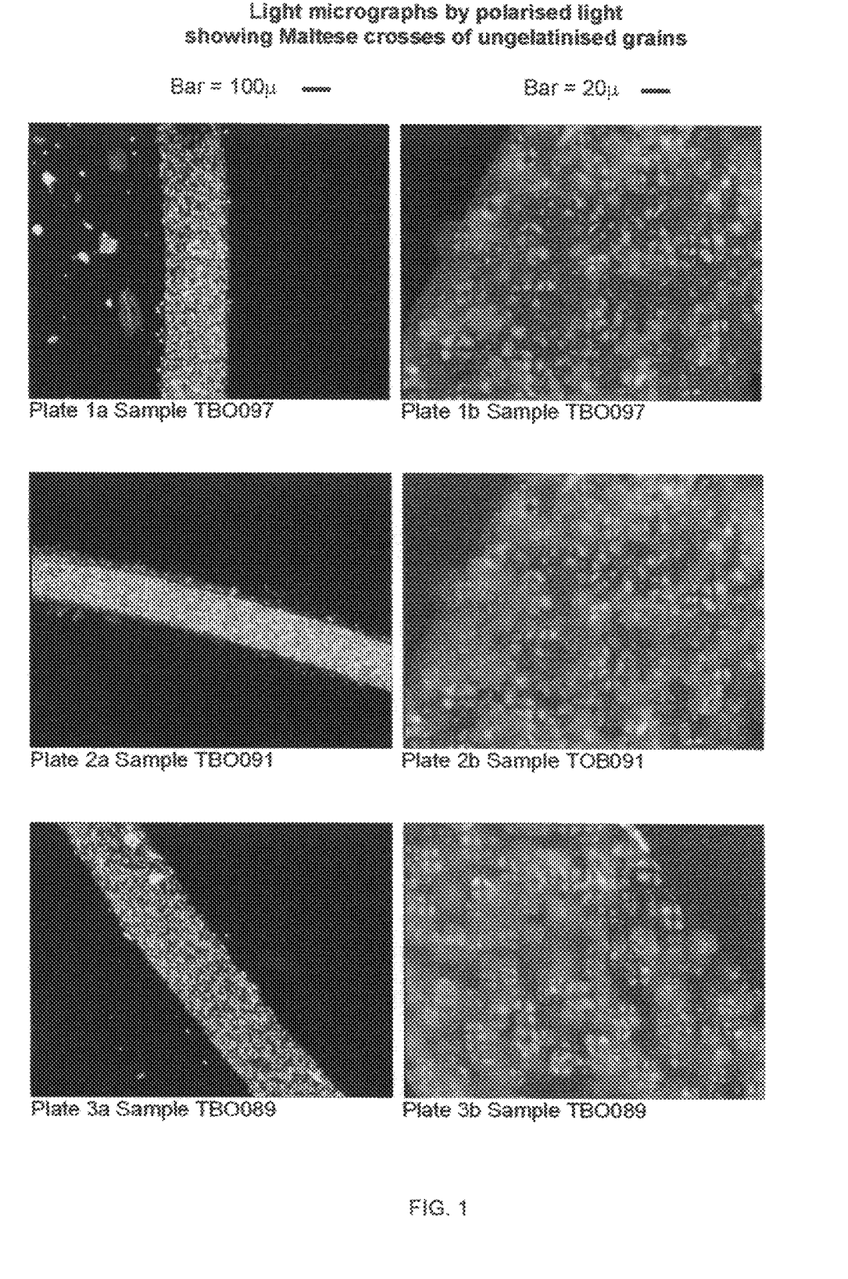
FIG. 1 is a series of representative samples according to the instant invention seen as polarized light micrographs showing "Maltese Crosses" of ungelatinized starch grains.
Figure 2:
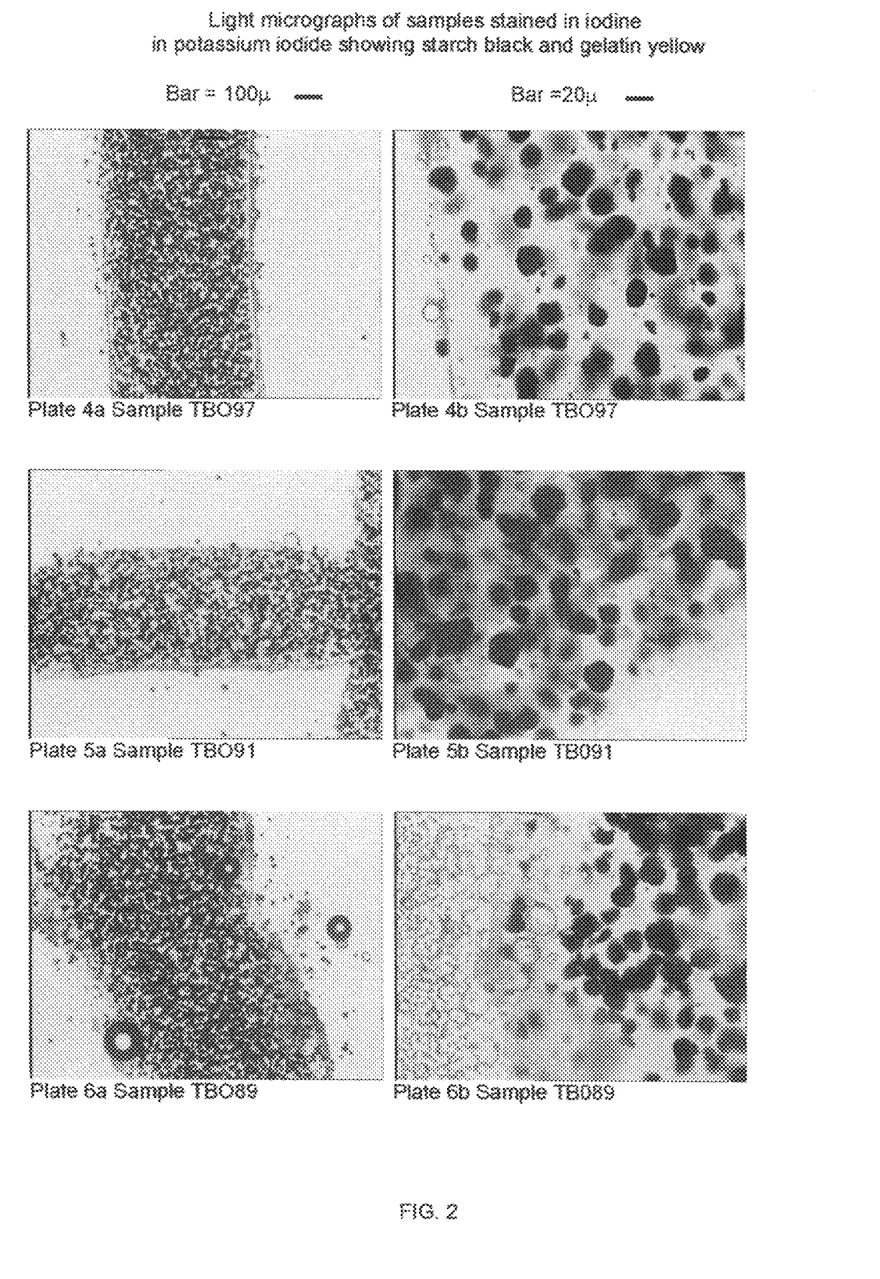
FIG. 2 is a series of representative samples according to the instant invention seen as light micrographs showing starch granules stained black with potassium iodide.

Polarized light micrographs, seen as FIG. 1, of representative samples according to the instant invention, show the typical "Maltese Cross" appearance of ungelatinized starch in the gelatin film matrix, due to the particular birefringence patterns exhibited by the crystalline starch granules. Light micrographs of representative samples stained with potassium iodide to stain starch granules black, seen in FIG. 2, show a relatively dense scattering of starch granules throughout the gelatin film matrix. Informal assessment of the amount of ungelatinized starch indicates that it may be near, or even in excess, of 50% of the total starch in the formulation.

Thinning of Gelatin Films

It is know in the art that thinner gelatin films have a faster oral dissolution, for gelatin of a given bloom strength, than thicker films, due to relative ease with which thinner films may be hydrated in the oral cavity. Also, as the bloom strength of a gelatin increases, so does the strength of ribbons cast form such gelatins. Accordingly, as gelatin strengths were increased by the use of higher bloom gelatins, simultaneous experimentation was undertaken with casting thinner gelatin films. This was in part accomplished by cooling the casting drums, using either water or cooled air, to temperatures ranging below 12° C., and preferably, in the range of from 8° C. to 10° C. Surprisingly, the use of stronger gelatins combined with the use of substantially ungelatinized starch as a water retention agent produced a relatively robust film, even at thinner ribbon thicknesses, as will be detailed below, and in some embodiments allowed the rotary die encapsulation machine to be run at speeds up to 3.5 RPM, well above the traditional limits of about 2.0 RPM seen with other soft chewable capsule formulations. Additionally, the capsules formed by the instant invention were found to have very robust seals, caused in part by the relatively large ratio of seal area to capsule wall thickness. For example, a capsule seal area spanning 0.010 inch represents one half the total wall thickness of a 0.020 thickness capsule, but only one-third the total wall thickness of a 0.030 thickness capsule.

Partial Drying to Relatively High End Water Content

Soft gelatin capsules are traditionally dried to an industry standard of 6%-10% end water content. Gelatin capsules are traditionally fabricated at water contents well above this level, and then dried, as for example, in U.S. Pat. No. 6,258,380 to Overholt, wherein capsules are initially as much as 30% water by weight, being subsequently dried to 6%-8% water. However, experimentation has shown that capsules of significantly greater water content had an improved mouth feel and chewability. It was noted that capsules with such high water contents tended to be sticky and to easily clump together. Testing of representative samples according to the instant invention showed a final end water content of approximately 9.5%-11.5%. Rather than expose these capsules to traditional forms of drying in a reduced humidity atmosphere, experimentation was directed to lightly tumble drying the capsules to the approximate end water content stated herein, and then applying various surface treatments, detailed below, to ameliorate the structural effects of high water content encapsulation.

These surface treatments may involve an effective anti-stickiness coating, in the form of a dusting agent, that would decrease the surface stickiness of the capsules without the necessity of lowering the water content thereof. Such surface treatments may include a plurality of dry agents, such as starches, or may include various waxes and liquid applications. The surface treatment agents may be inert, designed solely to combat stickiness, may act to enhance, complement, or ameliorate some aspect of the capsule fill, or may simply act as a desirable flavoring agent for the capsule. Attention is also directed to the use of coatings or dusting agents bearing active ingredients, which may multiply the number and types of agents that can be transmitted as part of these dosage forms.

Surface Treatment

After the tumble dry process, the capsules are transferred into either a polishing pan or an automated inline dusting system whereby the product is coated with a layer of starch, typically potato or corn starch, although tapioca starch, wheat powder, waxy corn starch powder, and partial alpha starch powder are also effective. The capsules are then tumbled to produce an even coating of starch which minimizes the capsules sticking to one another. Agents may also be applied by electrostatic coating processes, and as detailed previously, and may include wax, liquid, polyol or other substances used in place of a dry dusting agent.

After tumbling, the capsules are transferred onto a vibratory sieve where they are vibrated to remove excess coating material. The product is then passed through a metal detector to minimize chances for product contamination, and then bulk packaged. While there is significant stickiness of the capsules without starch, a starch level of 0.5% provides good results in preventing capsule sticking.

Surprisingly, it was found that certain relatively small capsules, such as, for example 4 Round capsules, with certain fills, may not need any drying before the application of surface treatments. In such cases, considerable savings in processing times and costs may be had by directly moving such capsules from fabrication to surface treatment, and then to packaging; thus eliminating the traditional drying step.

EXPERIMENT 1

TABLE 1

Initial Capsule Formulation; Experiment 1

| Material | % in Melt |
|---|---|
| 200 Bloom Fish Gelatin | 29.0 |
| Glycerin | 33.0 |
| Modified Starch | 11.0 |
| Purified Water | 27.0 |

Experimentation directed to a higher than normal water content gelatin capsule was undertaken with a fish gelatin exhibiting a moderate bloom strength (200 bloom). In subsequent experiments, gelatin of relatively high bloom strength (275 bloom) was also found to give excellent results. Subject gelatin was mixed in a mixing unit to maintain process temperatures. The proportional quantity of purified water was transferred to the unit and heated to 55° C. Under vacuum, the proportional amount of required fish gelatin was transferred to the heated purified water. The mass was maintained at 55° C. and mixed until a clear solution was obtained, which was approximately 30 minutes. In a separate vessel, the required quantity of starch or starches, and by way of example and not limitation, hydroxypropylated starch was found to work well; was added to the required amount of plasticizer (glycerin), the plasticizer/glycerin slurry mixed, and the slurry transferred to the fish gel. Other suitable plasticizers include, but are not limited to: sorbitol, polyethylene glycol, sucrose, mannitol, corn syrup, fructose, cellulose, dioctyl-sodium sulfosuccinate, triethyl citrate, tributyl citrate, 1,2-propylenglycol, mono-, di- or triacetates of glycerol, and natural gum. The resulting mass was continuously stirred and heated until the temperature of the product had reached 55° C. Vacuum was applied to de-aerate the mass, and the mass was transferred into a suitable jacketed vessel, maintaining the product temperature between 50° C. and 55° C. Optional colors, flavors, and sweeteners were added using a blender.

The gelatin mass was fabricated using a rotary die encapsulation machine with spreader boxes maintained at 38° C. to 45° C., the casting drums cooled to between 8° C. and 12° C., and the injection wedge maintained at a temperature of 28° C. to 35° C. The rotary die encapsulation machine was run at varying machine speeds of up to 2.5 RPM and, using automatic leveling guide bars, ribbon thickness was maintained at 0.025-0.028 inches. It was found that this formulation did not perform well in peeling from the casting drums at higher speeds or thinner ribbon thicknesses. Formed capsules were tumble dried to reduce the water activity to between 38%-45% (Aw 0.38-0.45). Time in the drier varied according to the capsule size and shell mass, being on the order of 10-12 minutes for 4 Round capsules and up to 12-15 minutes for 16 Oval capsules. After the tumble dry process, the capsules are transferred into either a polishing pan or an automated inline dusting system whereby the product is coated with a layer of starch, typically potato or corn starch, although tapioca starch, wheat powder, waxy corn starch powder, and partial alpha starch powder are also effective. In particular, a fine grade tapioca starch gave excellent results. The capsules are then tumbled to produce an even coating of starch which prevents the capsules from sticking to one another. In addition to the dusting materials illustrated above, dusting materials may incorporate active ingredients. Such active ingredients may, in the case of medicated capsules, include such medications as to enhance, complement or ameliorate some aspect of the medicated filling of the capsule. In the case of non-medicated capsules, such as, by way of illustration and not limitation, include flavorings and mouth cooling agents. In addition, as it is well know in the art that certain flavoring compounds tend to effect the structure of the capsules themselves, such as, for example, increasing the cross-linking of the gelatin chains in the capsule shells; such flavorings may be selected from flavorings or other groups known to minimize this cross-linking effect, and thereby tend to increase the stability of the product.

Capsules are dusted with starch at approximately 5 gms of starch per 2-4/kg of product. An inline automated dusting system maybe employed to automate the dusting process, with machine dusting levels regulated by predetermined parameters related to capsule size. The capsules are transferred onto a vibratory sieve where they are vibrated to remove excess coating material. The product is then passed through a metal detector to minimize chances for product contamination, and then bulk packaged.

TABLE 2

Experiment 1; Gelatin, Batch Details, Fabrication Parameters

| Batch No. | Gelatin | Batch Details | Parameters |
|---|---|---|---|
| TB072 | 200 Bloom Fish Gelatin | 4 Round flavored oil fill | 250 mg fill, 106 mg/ 0.025"/ribbon, 2.5 RPM |
| TB073 | 200 Bloom Fish Gelatin | 4 Round flavored oil fill | 250 mg fill, 106 mg/ 0.015"/ribbon, 2.5 RPM |
| TB074 | 200 Bloom Fish Gelatin | 4 Round flavored oil fill | 250 mg fill, 106 mg/ 0.025"/ribbon, 2.5 RPM |
| TB075 | 200 Bloom Fish Gelatin | 4 Round flavored oil fill | 250 mg fill, 106 mg/ 0.025"/ribbon, 2.5 RPM |
| TB076 | 200 Bloom Fish Gelatin | 4 Round flavored oil fill | 250 mg fill, 106 mg/ 0.025"/ribbon, 2.5 RPM |
| TB077 | 200 Bloom Fish Gelatin | 4 Round flavored oil fill | 250 mg fill, 106 mg/ 0.025"/ribbon, 2.5 RPM |
| TB078 | 200 Bloom Fish Gelatin | 4 Round flavored oil fill | 250 mg fill, 106 mg/ 0.025"/ribbon, 2.5 RPM |
| TB079 | 200 Bloom Fish Gelatin | 4 Round flavored oil fill | 250 mg fill, 106 mg/ 0.025"/ribbon, 2.5 RPM |

Initial measurements were made of capsules appearance as to conformation with product design, rupture time, disintegration, equilibrium relative humidity and water activity. Conformation was assessed visually, with capsules adjudged conforming if they retained their originally fabricated shape and texture. Capsule disintegration and rupture time were assessed according to the testing method specified by the European Pharmacopoeia 4th Edition. Rupture time is defined as the time taken for the capsule seal to be opened and a visible quantity of the liquid content to be seen coming out from the shell. Disintegration time is defined as the time taken for the entire gelatin capsule shell to dissolve in the water medium.

A Rotronic (available form Rotronic AG; Switzerland) water activity meter was used to determine end relative humidity (ERH) and water activity. Capsules were placed on stability in sealed amber jars at varying temperatures and relative humidity, and periodically tested according to the same testing parameters.

TABLE 3

Experiment 1; Stability Data 1–8 weeks Chewable Fish Gel (Batch TB072)

| Timepoint | Conditions | Appearance | Rupture Time (min) | Disintegration (min) | ERH (%) | Water Activity |
|---|---|---|---|---|---|---|
| 0 | Initial | Conforms | 0.3 | 2.0 | 42.5 | 0.43 |
| 1 wk | 25° C./60% RH | Conforms | 0.2 | 2.2 | 43.1 | 0.43 |
| 2 wks | 25° C./60% RH | Slight Clumping | 0.3 | 2.1 | 43.6 | 0.44 |
| 4 wks | 25° C./60% RH | Conforms | 0.3 | 2.7 | 42.5 | 0.43 |
| 8 wks | 25° C./60% RH | Conforms | 0.4 | 2.5 | 43.8 | 0.44 |
| 1 wk | 30° C./65% RH | Conforms | 0.2 | 2.4 | 43.0 | 0.43 |
| 2 wks | 30° C./65% RH | Conforms | 0.4 | 2.6 | 44.0 | 0.44 |
| 4 wks | 30° C./65% RH | Slight Clumping | 0.4 | 2.1 | 44.9 | 0.45 |
| 8 wks | 30° C./65% RH | Slight Clumping | 0.5 | 2.5 | 43.3 | 0.43 |

TABLE 4

Experiment 1; Stability Data 1–8 weeks Chewable Fish Gel (Batch TB073)

| Timepoint | Conditions | Appearance | Rupture Time (min) | Disintegration (min) | ERH (%) | Water Activity |
|---|---|---|---|---|---|---|
| 0 | Initial | Conforms | 0.3 | 2.2 | 42.2 | 0.42 |
| 1 wk | 25° C./60% RH | Conforms | 0.2 | 2.3 | 43.0 | 0.43 |
| 2 wks | 25° C./60% RH | Conforms | 0.3 | 2.6 | 44.2 | 0.44 |
| 4 wks | 25° C./60% RH | Conforms | 0.4 | 2.7 | 46.7 | 0.47 |
| 8 wks | 25° C./60% RH | Conforms | 0.4 | 2.5 | 47.5 | 0.48 |
| 1 wk | 30° C./65% RH | Conforms | 0.3 | 2.5 | 42.9 | 0.43 |
| 2 wks | 30° C./65% RH | Conforms | 0.4 | 2.5 | 43.5 | 0.44 |
| 4 wks | 30° C./65% RH | Slight Clumping | 0.6 | 2.6 | 44.6 | 0.45 |
| 8 wks | 30° C./65% RH | Conforms | 0.4 | 2.6 | 43.4 | 0.43 |

TABLE 5

Experiment 1; Stability Data 1–8 weeks Chewable Fish Gel (Batch TB074)

| Timepoint | Conditions | Appearance | Rupture Time (min) | Disintegration (min) | ERH (%) | Water Activity |
|---|---|---|---|---|---|---|
| 0 | Initial | Conforms | 0.2 | 2.4 | 42.1 | 0.42 |
| 1 wk | 25° C./60% RH | Conforms | 0.2 | 2.5 | 42.3 | 0.42 |
| 2 wks | 25° C./60% RH | Conforms | 0.2 | 2.3 | 45.5 | 0.46 |
| 4 wks | 25° C./60% RH | Conforms | 0.4 | 2.4 | 44.1 | 0.44 |
| 8 wks | 25° C./60% RH | Conforms | 0.4 | 2.4 | 47.3 | 0.47 |
| 1 wk | 30° C./65% RH | Conforms | 0.3 | 2.7 | 42.5 | 0.43 |
| 2 wks | 30° C./65% RH | Conforms | 0.7 | 3.1 | 44.2 | 0.44 |
| 4 wks | 30° C./65% RH | Conforms | 0.5 | 2.6 | 45.1 | 0.45 |
| 8 wks | 30° C./65% RH | Conforms | 0.4 | 2.5 | 50.3 | 0.50 |

TABLE 6

Experiment 1; Stability Data 1–8 weeks Chewable Fish Gel (Batch TB075)

| Timepoint | Conditions | Appearance | Rupture Time (min) | Disintegration (min) | ERH (%) | Water Activity |
|---|---|---|---|---|---|---|
| 0 | Initial | Conforms | 0.2 | 2.4 | 41.8 | 0.42 |
| 1 wk | 25° C./60% RH | Conforms | 0.3 | 2.4 | 42.3 | 0.42 |

TABLE 6-continued

Experiment 1; Stability Data 1–8 weeks Chewable Fish Gel (Batch TB075)

| Timepoint | Conditions | Appearance | Rupture Time (min) | Disintegration (min) | ERH (%) | Water Activity |
|---|---|---|---|---|---|---|
| 2 wks | 25° C./60% RH | Conforms | 0.4 | 2.6 | 42.9 | 0.43 |
| 4 wks | 25° C./60% RH | Conforms | 0.4 | 2.6 | 44.1 | 0.44 |
| 8 wks | 25° C./60% RH | Conforms | 0.4 | 2.5 | 46.0 | 0.46 |
| 1 wk | 30° C./65% RH | Conforms | 0.5 | 2.5 | 42.5 | 0.43 |
| 2 wks | 30° C./65% RH | Conforms | 0.4 | 2.7 | 44.4 | 0.44 |
| 4 wks | 30° C./65% RH | Conforms | 0.6 | 2.7 | 45.2 | 0.45 |
| 8 wks | 30° C./65% RH | Slight Clumping | 0.6 | 2.5 | 45.0 | 0.45 |

TABLE 7

Experiment 1; Stability Data 1–8 weeks Chewable Fish Gel (Batch TB076)

| Timepoint | Conditions | Appearance | Rupture Time (min) | Disintegration (min) | ERH (%) | Water Activity |
|---|---|---|---|---|---|---|
| 0 | Initial | Conforms | 0.3 | 1.4 | 39.3 | 0.40 |
| 1 wk | 25° C./60% RH | Conforms | 0.4 | 1.9 | 40.6 | 0.41 |
| 2 wks | 25° C./60% RH | Conforms | 0.3 | 2.1 | 42.5 | 0.43 |
| 4 wks | 25° C./60% RH | Conforms | 0.3 | 2.0 | 43.9 | 0.44 |
| 8 wks | 25° C./60% RH | Conforms | 0.5 | 1.9 | 44.9 | 0.45 |
| 1 wk | 30° C./65% RH | Conforms | 0.4 | 1.7 | 39.6 | 0.40 |
| 2 wks | 30° C./65% RH | Conforms | 0.4 | 2.0 | 41.2 | 0.41 |
| 4 wks | 30° C./65% RH | Conforms | 0.4 | 2.5 | 44.5 | 0.45 |
| 8 wks | 30° C./65% RH | Conforms | 0.7 | 1.8 | 45.6 | 0.46 |

TABLE 8

Experiment 1; Stability Data 1–8 weeks Chewable Fish Gel (Batch TB077)

| Timepoint | Conditions | Appearance | Rupture Time (min) | Disintegration (min) | ERH (%) | Water Activity |
|---|---|---|---|---|---|---|
| 0 | Initial | Conforms | 0.4 | 1.6 | 39.0 | 0.39 |
| 1 wk | 25° C./60% RH | Conforms | 0.3 | 1.8 | 39.4 | 0.39 |
| 2 wks | 25° C./60% RH | Conforms | 0.4 | 1.8 | 40.9 | 0.41 |
| 4 wks | 25° C./60% RH | Conforms | 0.4 | 2.0 | 45.9 | 0.46 |
| 8 wks | 25° C./60% RH | Conforms | 0.4 | 1.6 | 41.2 | 0.41 |
| 1 wk | 30° C./65% RH | Conforms | 0.4 | 1.7 | 38.9 | 0.39 |
| 2 wks | 30° C./65% RH | Conforms | 0.5 | 1.7 | 46.0 | 0.46 |
| 4 wks | 30° C./65% RH | Conforms | 0.4 | 2.1 | 41.2 | 0.41 |
| 8 wks | 30° C./65% RH | Conforms | 0.5 | 1.6 | 42.5 | 0.43 |

TABLE 9

Experiment 1; Stability Data 1–8 weeks Chewable Fish Gel (Batch TB078)

| Timepoint | Conditions | Appearance | Rupture Time (min) | Disintegration (min) | ERH (%) | Water Activity |
|---|---|---|---|---|---|---|
| 0 | Initial | Conforms | 0.3 | 1.7 | 38.2 | 0.38 |
| 1 wk | 25° C./60% RH | Conforms | 0.3 | 1.5 | 39.1 | 0.39 |
| 2 wks | 25° C./60% RH | Conforms | 0.4 | 2.1 | 40.2 | 0.40 |
| 4 wks | 25° C./60% RH | Conforms | 0.3 | 1.8 | 45.1 | 0.45 |
| 8 wks | 25° C./60% RH | Conforms | 0.5 | 1.7 | 41.8 | 0.42 |
| 1 wk | 30° C./65% RH | Conforms | 0.5 | 1.7 | 38.4 | 0.38 |
| 2 wks | 30° C./65% RH | Conforms | 0.4 | 1.9 | 40.7 | 0.41 |
| 4 wks | 30° C./65% RH | Conforms | 0.5 | 1.9 | 41.3 | 0.41 |
| 8 wks | 30° C./65% RH | Conforms | 0.7 | 2.0 | 42.2 | 0.42 |

TABLE 10

Experiment 1; Stability Data 1–8 weeks Chewable Fish Gel (Batch TB079)

| Timepoint | Conditions | Appearance | Rupture Time (min) | Disintegration (min) | ERH (%) | Water Activity |
|---|---|---|---|---|---|---|
| 0 | Initial | Conforms | 0.4 | 1.4 | 39.0 | 0.39 |
| 1 wk | 25° C./60% RH | Conforms | 0.4 | 1.6 | 39.4 | 0.39 |
| 2 wks | 25° C./60% RH | Conforms | 0.3 | 2.3 | 40.7 | 0.41 |
| 4 wks | 25° C./60% RH | Conforms | 0.3 | 1.8 | 41.5 | 0.42 |
| 8 wks | 25° C./60% RH | Conforms | 0.5 | 1.7 | 44.5 | 0.45 |
| 1 wk | 30° C./65% RH | Conforms | 0.4 | 1.8 | 39.4 | 0.39 |
| 2 wks | 30° C./65% RH | Conforms | 0.3 | 2.0 | 40.2 | 0.40 |
| 4 wks | 30° C./65% RH | Conforms | 0.3 | 1.9 | 41.1 | 0.41 |
| 8 wks | 30° C./65% RH | Conforms | 0.5 | 1.7 | 40.0 | 0.40 |

The gelatin capsules presented excellent test qualities such as fast rupture and quick dissolution, that tend to predict good organoleptic qualities. Slight prolongation of rupture time and disintegration times over initial values were seen over the 8 week stability testing program. Stability of hydration, as measured by equilibrium relative humidity and water activity were relatively constant across all tested samples. There was difficulty in maintaining capsules at the highest temperature and highest relative humidity conditions tested. Under storage conditions of 35° C. and 60% RH, the capsules tended to clump together, and in some formulations, even to melt. As even severe clumping less than melting is commercially disadvantageous, and as capsules are desired to withstand the most rigorous storage conditions, additional experiments were undertaken in attempts to strengthen the capsules for such severe storage conditions, without losing the desirable organoleptic properties seen in Experiment 1.

EXPERIMENT 2

Experimentation was undertaken to change gelatin compositions, but to otherwise maintain the formulation proportions of Experiment 1. Accordingly, compositions in which gelatin comprised 29% w/w of the melt, utilizing 275 bloom strength fish gelatin (Batches TB087-89), 150 bloom limed bovine hide gelatin (Batches TB090-92), and a combination of 275 bloom strength fish gelatin (8% of total composition) and 150 bloom limed bovine hide gelatin (21% of total composition) were tested. Capsules were formulated utilizing different fills, including Peppermint (Structured) Oil and Paste according to the following formulations:

TABLE 11

Experiment 2; Fill Formulations

| | Quantities in mg/capsule | | |
|---|---|---|---|
| Material | 2 Round Structured Oil Capsule | 4 Round Structured Oil Capsule | 16 Oval Paste |
| Medium Chain Triglycerides | 82 | 206 | 481 |
| Kaorich Beads | | | 49.8 |
| Loders 7 (Hard Vegetable Fat) | | | 213.76 |
| Lecithin Thin (light) | | | 12.84 |
| Levomenthol | | | 26.08 |
| Aspartame NF | 1 | 2 | 7.16 |
| Saccharin Sodium | | | .652 |
| Peppermint Oil | | | 8.708 |
| Mannitol BP/EP | | | 200 |
| Peppermint Flavor | 13 | 31 | |

TABLE 11-continued

Experiment 2; Fill Formulations

| | Quantities in mg/capsule | | |
|---|---|---|---|
| Material | 2 Round Structured Oil Capsule | 4 Round Structured Oil Capsule | 16 Oval Paste |
| Colloidal Silicon Dioxide | 3 | 8 | |
| Purified Water | 1 | 3 | |
| Total | 100 | 250 | 1000 |

TABLE 12

Experiment 2; Gelatins, Batch Details, Manufacturing Parameters

| Batch No. | Gelatin | Batch Details | Parameters |
|---|---|---|---|
| TB087 | 275 Bloom Fish Gelatin | 2 Round Peppermint Fish Gel Capsules | 100 mg fill, 45 mg/0.015" shell, 3 RPM |
| TB088 | 275 Bloom Fish Gelatin | 4 Round Peppermint Fish Gel Capsules | 250 mg fill, 64 mg/0.015" shell, 3 RPM |
| TB089 | 275 Bloom Fish Gelatin | 16 Oval Peppermint Paste Fish Gel Capsules | 1000 mg fill, 208 mg/0.015" shell, 3 RPM |
| TB090 | 150 Bloom Limed Bovine Hide Gelatin | 2 Round Peppermint Bovine Capsules | 100 mg fill, 45 mg/0.015" shell, 3 RPM |
| TB091 | 150 Bloom Limed Bovine Hide Gelatin | 4 Round Peppermint Bovine Capsules | 250 mg fill, 64 mg/0.015" shell, 3 RPM |
| TB092 | 150 Bloom Limed Bovine Hide Gelatin | 16 Oval Peppermint Paste Bovine Capsules | 1000 mg fill, 208 mg/0.015" shell, 3 RPM |
| TB095 | 275 Bloom Fish Gelatin (8%) 150 Bloom Limed Bovine Hide Gelatin (21%) | 2 Round Peppermint Fish & Bovine Blend | 100 mg fill, 45 mg/0.015" shell, 3 RPM |
| TB096 | 275 Bloom Fish Gelatin (8%) 150 Bloom Limed Bovine Hide Gelatin (21%) | 4 Round Peppermint Fish - Bovine Blend | 250 mg fill, 64 mg/0.015" shell, 3 RPM |
| TB097 | 275 Bloom Fish Gelatin (8%) 150 Bloom Limed Bovine Hide Gelatin (21%) | 16 Oval Peppermint Paste Fish - Bovine Blend | 1000 mg fill, 208 mg/0.015" shell, 3 RPM |

Subject gelatin or gelatins was mixed in a mixing unit to maintain process temperatures. The proportional quantity of purified water was transferred to the unit and heated to 55° C. Under vacuum, the proportional amount of required fish gelatin or gelatins was transferred to the heated purified water. The mass was maintained at 55° C. and mixed until a clear solution was obtained, which was approximately 30 minutes. In a separate vessel, the required quantity of starch or starches was added to the required amount of plasticizer (glycerin), the plasticizer/glycerin slurry mixed, and the slurry transferred to the gelatin mix. The resulting mass was continuously stirred and heated until the temperature of the product had reached 55° C. Vacuum was applied to de-aerate the mass, and the mass was transferred into a suitable jacketed vessel, maintaining the product temperature between 50° C. and 55° C. Optional colors, flavors, and sweeteners were added using a blender.

The gelatin mass was fabricated using a rotary die encapsulation machine with spreader boxes maintained at 38° C. to 45° C., the casting drums cooled to between 8° C. and 12° C., and the injection wedge maintained at a temperature of 28° C. to 35° C. The rotary die encapsulation machine was run at varying machine speeds of up to 3.5 RPM and, using automatic leveling guide bars, ribbon thickness was maintained as low as 0.015 inches. Formed capsules were tumble dried to reduce the water activity to between 38%-45% (Aw 0.38-0.45). Time in the drier varied according to the capsule size and shell mass, being on the order of 10-12 minutes for 4 Round capsules and up to 12-15 minutes for 16 Oval capsules. After the tumble dry process, the capsules are transferred into either a polishing pan or an automated inline dusting system whereby the product is coated with a layer of starch, typically potato or corn starch, although tapioca starch, wheat powder, waxy corn starch powder, and partial alpha starch powder are also effective. In particular, a fine grade tapioca starch gave excellent results. The capsules are then tumbled to produce an even coating of starch which prevents the capsules from sticking to one another. In addition to the dusting materials illustrated above, dusting materials may incorporate active ingredients. Such active ingredients may, in the case of medicated capsules, include such medications as to enhance, complement or ameliorate some aspect of the medicated filling of the capsule. In the case of non-medicated capsules, such as, by way of illustration and not limitation, include flavorings and mouth cooling agents. In addition, as it is well know in the art that certain flavoring compounds tend to effect the structure of the capsules themselves, such as, for example, increasing the cross-linking of the gelatin chains in the capsule shells; such flavorings may be selected from flavorings or other groups known to minimize this cross-linking effect, and thereby tend to increase the stability of the product.

Capsules are dusted with starch at approximately 5 gms of starch per 2-4/kg of product. An inline automated dusting system maybe employed to automate the dusting process, with machine dusting levels regulated by predetermined parameters related to capsule size. The capsules are transferred onto a vibratory sieve where they are vibrated to remove excess coating material. The product is then passed through a metal detector to minimize chances for product contamination, and then bulk packaged.

Initial measurements were made of capsules appearance as to conformation with product design, rupture time, disintegration, equilibrium relative humidity and water activity. Capsules were placed on stability in sealed amber jars at varying temperatures and relative humidity, and periodically tested according to the same testing parameters.

TABLE 13

Experiment 2: Stability Testing at 2 Weeks (Fish Gel)

| Batch No. | Conditions | Appearance | Rupture Time (min) | Disintegration (min) | ERH (%) | Water Activity |
|---|---|---|---|---|---|---|
| TB087 | Initial (Time = 0) | Conforms | 0.2 | 0.9 | 30.2 | 0.30 |
| TB087 | 25° C./60% RH | Conforms | 0.3 | 1.0 | 41.2 | 0.41 |
| TB087 | 30° C./65% RH | Conforms | 0.3 | 0.9 | 45.1 | 0.45 |
| TB087 | 35° C./60% RH | Conforms | 0.4 | 1.1 | 41.1 | 0.41 |
| TB087 | 40° C./75% RH | Slight Clumping | NT | NT | NT | NT |
| TB088 | Initial | Conforms | 0.2 | 1.2 | 28.9 | 0.29 |
| TB088 | 25° C./60% RH | Conforms | 0.2 | 0.9 | 32.2 | 0.32 |
| TB088 | 30° C./65% RH | Conforms | 0.2 | 0.9 | 35.0 | 0.35 |
| TB088 | 35° C./60% RH | | 0.3 | 0.9 | 38.6 | 0.39 |
| TB088 | 40° C./75% RH | Slight Clumping | NT | NT | NT | NT |
| TB089 | Initial | Conforms | 0.5 | 1.3 | 34.7 | 0.35 |
| TB089 | 25° C./60% RH | Conforms | 0.3 | 1.2 | 34.8 | 0.35 |
| TB089 | 30° C./65% RH | Slight Clumping | 0.5 | 1.4 | 35.5 | 0.36 |
| TB089 | 35° C./60% RH | Severe Clumping | 0.6 | 2.1 | 37.9 | 0.38 |
| TB089 | 40° C./75% RH | Melted | NT | NT | NT | NT |

TABLE 14

Experiment 2: Stability Testing at 2 Weeks* (Bovine Gel)

| Batch No. | Conditions | Appearance | Rupture Time | Disintegration | ERH (%) | Water Activity |
|---|---|---|---|---|---|---|
| TB090 | Initial | Conforms | 0.2 | 0.9 | 32.0 | 0.32 |
| TB090 | 25° C./60% RH | Conforms | 0.4 | 1.0 | 37.1 | 0.37 |
| TB090 | 30° C./65% RH | Conforms | 0.3 | 0.9 | 36.2 | 0.36 |
| TB090 | 35° C./60% RH | Conforms | 0.3 | 0.9 | 45.0 | 0.45 |
| TB090 | 40° C./75% RH | Severe Clumping | NT | NT | NT | NT |
| TB091 | Initial | Conforms | 0.2 | 1.3 | 30.1 | 0.30 |

TABLE 14-continued

Experiment 2; Stability Testing at 2 Weeks* (Bovine Gel)

| Batch No. | Conditions | Appearance | Rupture Time | Disintegration | ERH (%) | Water Activity |
|---|---|---|---|---|---|---|
| TB091 | 25° C./60% RH | Conforms | 0.3 | 1.0 | 33.3 | 0.33 |
| TB091 | 30° C./65% RH | Conforms | 0.3 | 1.0 | 37.4 | 0.37 |
| TB091 | 35° C./60% RH | Slight Clumping+ | 0.3 | 1.1 | 39.1 | 0.39 |
| TB091* | 40° C./75% RH | Slight Clumping+ | 0.8 | 1.7 | 43.9 | 0.44 |
| TB092 | Initial | Conforms | 0.4 | 2.0 | 36.4 | 0.36 |
| TB092 | 25° C./60% RH | Conforms | 0.6 | 2.0 | 36.3 | 0.36 |
| TB092 | 30° C./65% RH | Slight Clumping | 0.7 | 1.8 | 40.7 | 0.41 |
| TB092 | 35° C./60% RH | Slight Clumping | 0.8 | 2.1 | 38.9 | 0.39 |
| TB092 | 40° C./75% RH | Melted | NT | NT | NT | NT |

+Air Bubble in Fill
*Batch TB091 at 40° C./75% RH tested at 3 weeks due to measuring error at 2 weeks

TABLE 15

Experiment 2; Stability Testing at 2 Weeks (Fish and Bovine Gel)

| Batch No. | Conditions | Appearance | Rupture Time | Disintegration | ERH (%) | Water Activity |
|---|---|---|---|---|---|---|
| TB095 | Initial | Conforms | 0.1 | 1.0 | 29.6 | 0.30 |
| TB095 | 25° C./60% RH | Conforms | 0.3 | 1.4 | 26.1 | 0.26 |
| TB095 | 30° C./65% RH | Conforms | 0.5 | 1.1 | 28.2 | 0.28 |
| TB095 | 35° C./60% RH | Conforms | 0.4 | 1.1 | 46.7 | 0.47 |
| TB095 | 40° C./75% RH | Slight Clumping | NT | NT | NT | NT |
| TB096 | Initial | Conforms | 0.1 | 1.0 | 29.6 | 0.30 |
| TB096 | 25° C./60% RH | Conforms | 0.3 | 1.3 | 31.2 | 0.31 |
| TB096 | 30° C./65% RH | Conforms | 0.3 | 1.1 | 34.1 | 0.34 |
| TB096 | 35° C./60% RH | Conforms | 0.5 | 1.2 | 33.6 | 0.34 |
| TB096 | 40° C./75% RH | Slight Clumping | NT | NT | NT | NT |
| TB097 | Initial | Conforms | 0.3 | 1.7 | 36.6 | 0.37 |
| TB097 | 25° C./60% RH | Conforms | 0.4 | 2.1* | 36.7 | 0.37 |
| TB097 | 30° C./65% RH | Slight Clumping | 0.7 | 2.1* | 43.1 | 0.43 |
| TB097 | 35° C./60% RH | Slight Clumping | 1.3 | 2.2* | 38.1 | 0.38 |
| TB097 | 40° C./75% RH | Melting | NT | NT | NT | NT |

*Time for Gel to Melt. The Fill Remained as a Lump but Dissolved Within 5 Minutes

TABLE 16

Experiment 2; Stability Testing at 4 Weeks (Fish Gel)

| Batch No. | Conditions | Appearance | Rupture Time (min) | Disintegration (min) | ERH (%) | Water Activity |
|---|---|---|---|---|---|---|
| TB087 | Initial | Conforms | 0.2 | 0.9 | 30.2 | 0.30 |
| TB087 | 25° C./60% RH | Conforms | 0.3 | 0.9 | 49.5 | 0.50 |
| TB087 | 30° C./65% RH | Conforms | 0.4 | 0.9 | 51.7 | 0.52 |
| TB087 | 35° C./60% RH | Conforms | 0.5 | 1.0 | 47.8 | 0.48 |
| TB087 | 40° C./75% RH | Melted | NT | NT | NT | NT |
| TB088 | Initial | Conforms | 0.2 | 1.2 | 28.9 | 0.29 |
| TB088 | 25° C./60% RH | Conforms | 0.3 | 1.0 | 35.8 | 0.36 |
| TB088 | 30° C./65% RH | Conforms | 0.3 | 0.8 | 45.0 | 0.45 |
| TB088 | 35° C./60% RH | Slight Clumping | 0.5 | 1.0 | 40.4 | 0.40 |
| TB088 | 40° C./75% RH | Melted | NT | NT | NT | NT |
| TB089 | Initial | Conforms | 0.5 | 1.3 | 34.7 | 0.35 |
| TB089 | 25° C./60% RH | Conforms | 0.4 | 1.5 | 35.5 | 0.36 |
| TB089 | 30° C./65% RH | Slight Clumping | 0.7 | 1.5 | 36.2 | 0.36 |
| TB089 | 35° C./60% RH | Severe Clumping | NT | NT | NT | NT |
| TB089 | 40° C./75% RH | Melted | NT | NT | NT | NT |

TABLE 17

Experiment 2; Stability Testing at 4 Weeks (Bovine Gel)

| Batch No. | Conditions | Appearance | Rupture Time | Disintegration | ERH (%) | Water Activity |
|---|---|---|---|---|---|---|
| TB090 | Initial | Conforms | 0.2 | 0.9 | 32.0 | 0.32 |
| TB090 | 25° C./60% RH | Conforms | 0.4 | 1.0 | 35.6 | 0.36 |

TABLE 17-continued

Experiment 2; Stability Testing at 4 Weeks (Bovine Gel)

| Batch No. | Conditions | Appearance | Rupture Time | Disintegration | ERH (%) | Water Activity |
|---|---|---|---|---|---|---|
| TB090 | 30° C./65% RH | Conforms | 0.3 | 0.9 | 38.8 | 0.39 |
| TB090 | 35° C./60% RH | Conforms | 0.6 | 1.3 | 47.1 | 0.47 |
| TB090 | 40° C./75% RH | Severe Clumping | NT | NT | NT | NT |
| TB091 | Initial | Conforms | 0.2 | 1.3 | 30.1 | 0.30 |
| TB091 | 25° C./60% RH | Conforms | 0.2 | 1.2 | 34.9 | 0.35 |
| TB091 | 30° C./65% RH | Conforms | 0.4 | 1.2 | 33.8 | 0.34 |
| TB091 | 35° C./60% RH | Slight Clumping | 0.6 | 1.6 | 40.9 | 0.41 |
| TB091 | 40° C./75% RH | Slight Clumping | 0.5 | 1.6 | 37.6 | 0.38 |
| TB092 | Initial | Conforms | 0.4 | 2.0 | 36.4 | 0.36 |
| TB092 | 25° C./60% RH | Conforms | 0.3 | 2.0 | 39.7 | 0.40 |
| TB092 | 30° C./65% RH | Slight Clumping+ | 0.9 | 2.2 | 37.0 | 0.37 |
| TB092 | 35° C./60% RH | Slight Clumping+ | 1.4 | 2.2 | 45.0 | 0.45 |
| TB092 | 40° C./75% RH | Melted | NT | NT | NT | NT |

+Air Bubble in Fill

TABLE 18

Experiment 12; Stability Testing at 4 Weeks (Fish and Bovine Gel)

| Batch No. | Conditions | Appearance | Rupture Time | Disintegration | ERH (%) | Water Activity |
|---|---|---|---|---|---|---|
| TB095 | Initial | Conforms | 0.1 | 1.0 | 29.6 | 0.30 |
| TB095 | 25° C./60% RH | Conforms | 0.4 | 1.2 | 24.3 | 0.24 |
| TB095 | 30° C./65% RH | Conforms | 0.3 | 1.2 | 23.5 | 0.24 |
| TB095 | 35° C./60% RH | Conforms | 0.4 | 1.3 | 34.8 | 0.35 |
| TB095 | 40° C./75% RH | Slight Clumping | 0.7 | 1.7 | 47.1 | 0.47 |
| TB096 | Initial | Conforms | 0.1 | 1.0 | 29.6 | 0.30 |
| TB096 | 25° C./60% RH | Conforms | 0.4 | 1.1 | 33.1 | 0.33 |
| TB096 | 30° C./65% RH | Conforms | 0.3 | 1.1 | 32.2 | 0.32 |
| TB096 | 35° C./60% RH | Conforms | 0.6 | 1.3 | 37.1 | 0.37 |
| TB096 (3 weeks) | 40° C./75% RH | Severe Clumping | NT | NT | NT | NT |
| TB097 | Initial | Conforms | 0.3 | 1.7 | 36.6 | 0.37 |
| TB097 | 25° C./60% RH | Conforms | 0.7 | 4.1*** | 37.4 | 0.37 |
| TB097 | 30° C./65% RH | Slight Clumping | 1.0 | 4.8*** | 37.7 | 0.38 |
| TB097 | 35° C./60% RH | Slight Clumping | 1.2 | 5.6*** | 40.3 | 0.40 |
| TB097 | 40° C./75% RH | Melting | NT | NT | NT | NT |

***Time for Fill and Gel to Melt (See "Results and Evaluation of Experiment 2)

Results and Evaluation of Experiment 2

The gelatin capsules presented excellent test qualities such as fast rupture and quick dissolution, that tend to predict good organoleptic qualities, similar to those seen with the capsules prepared in Experiment 1. Slight prolongation of rupture time and disintegration times over initial values were seen in some embodiments over the 4 week stability testing program. Hydration, as measured by equilibrium relative humidity and water activity tended to increase with time across all tested samples. There was difficulty in maintaining capsules at the highest temperature and highest relative humidity conditions tested. The failure of capsules containing only gelatin derived from fish led in part to the testing of bovine and fish/bovine combinations. There was improvement is this aspect compared with Experiment 1. In improvement over the results of Experiment 1, most embodiments were able to survive storage conditions of 35° C. and 60% RH, with some surviving storage conditions of 40° C. and 75% RH. In particular, lots TB091 (4 Round bovine gelatin with peppermint oil fill) and TB095 (2 Round fish and bovine combination with peppermint oil fill) retained acceptable test parameters at this highest test temperature/RH.

Interestingly, higher bloom strength was not associated with a great deal of difference in the performance characteristics of the capsules, suggesting that the effect of the starch, in this case the substantially ungelatinized starch, has a greater effect than heretofore believed.

At the outset, the use of higher bloom strength gelatin in Experiment 2 suggested the possibility of casting ribbons that are significantly thinner than the traditional ribbon used in a rotary die encapsulation process. As noted above, in Experiment 2 the rotary die encapsulation machine was run at varying machine speeds of up to 3.5 RPM and, using automatic leveling guide bars, ribbon thickness was maintained as low as 0.015 inches.

This was expected to necessarily lead to a higher shell to fill ratio; that is, because the capsule wall are thinner, more fill material, and less gelation capsule wall material, is included with each oral dose. Measurement confirmed this, as seen in Table 19.

TABLE 19

Shell to Fill Ratios* of Thin Walled Capsules of the Instant Invention

| Size | Instant Invention Thin Ribbon Ratio | Standard Gelatin Ribbon Ratio |
|---|---|---|
| 2 round | 1:2.5–2.8 | 1:2–2.6 |
| 4 round | 1:4.5–4.8 | 1:2.2–2.6 |
| 16 oval | 1:5.5–59 | 1:2.5–3.0 |

*Standardized density fill used in all sample

This higher shell to fill ratio leads to a lower mass of gelatin associated with each oral dose, therefore leading to a more rapid and easier break up of the capsules in the oral cavity compared to a standard chewable shell. An organoleptic taste panel is provided with samples, in a double blind taste test. All capsules are unlabeled and are filled with the same peppermint compound,. Varying capsules sizes produced by the thin film technique of the instant invention and by a standard encapsulation process suing traditional thickness ribbons are tasted in a random manner. Tasters report that the thin film capsules generally have improved organoleptic properties such as better mouth texture, enhanced ease of dissolution, and less feel of gelatin mass in the mouth.

Despite considerable differences in formulation, taste panels report favorably on the capsules of the instant invention compared with those fabricated according to the method of co-owned U.S. Utility patent application Ser. No. 10/456,450 to Makino. In relation to the capsules of Makino, it was observed that the capsules of the instant invention displayed a 26.8% expansion during softening, compared with a 0.7% expansion during softening for the Makino capsules, which may in part account for excellent organoleptic qualities. Additionally, the instant capsules displayed softening over a range of $_{34}$-139° C., compared to a softening range of 44-77° C. for the capsules according to Makino.

INDUSTRIAL APPLICABILITY

The method and material of the instant invention enables a gelatin capsule to be formed that has good organoleptic properties, such as easy rupture and good mouth feel upon chewing, as well as giving satisfactory stability under predetermined storage times and conditions. The utilization of higher than normal bloom strength gelatin combined with substantially ungelatinized starch enables capsules to be fabricated form ribbons, using a traditional rotary die encapsulation method, that are considerably thinner than those heretofore used. Such capsules are both soft and chewable, and have a significantly lower shell to fill mass ratio, resulting in a smaller amount of capsule material associated with each oral dose. The capsules permit the pleasant and effective dosing, in the oral cavity, of a wide range of medicaments and foodstuffs.

We claim:

1. A finished soft gelatin capsule ready for packaging, comprising a capsule shell formed from a capsule film having a thickness not exceeding about 0.025 inches,
   wherein the capsule shell has an end composition comprising:
   at least one gelatin of about 275 bloom in about 20-55 weight % gelatin;
   plasticizer in about 19-40 weight %; and
   at least one hydroxypropylated starch in about 5-35 weight %, wherein the at least one hydroxypropylated starch is near, or in excess of, 50% ungelatinized; and
   a water content of 9.5-11.5 weight %, wherein the capsule shell is processed at a temperature no greater than 65° C.,
   wherein the finished soft gelatin capsule is edible and chewable, and
   wherein the finished soft gelatin capsule ruptures in an oral cavity.

2. The capsule of claim 1, wherein the plasticizer comprises at least glycerin.

3. The capsule of claim 1, wherein the plasticizer comprises at least sorbitol.

4. The capsule of claim 1, wherein the plasticizer is selected from the group consisting of polyethylene glycol, sucrose, mannitol, corn syrup, fructose, cellulose, dioctylsodium sulfosuccinate, triethyl citrate, tributyl citrate, 1,2-propylenglycol, mono-, di-or triacetates of glycerol, and natural gum.

5. The capsule of claim 1, wherein the at least one gelatin comprises about 25-40 weight % of the capsule.

6. The capsule of claim 1, wherein the at least one hydroxypropylated starch comprises 7-30 weight % of the capsule.

7. The capsule of claim 1, wherein the at least one gelatin is a bovine gelatin.

8. The capsule of claim 1, wherein the at least one gelatin is a combination of fish and bovine gelatins.

9. The capsule of claim 8, wherein fish gelatin comprises about 5-95 weight % and bovine gelatin comprises about 5-95 weight % of the capsule.

10. The capsule of claim 8, wherein the combination of gelatins comprises about 25-35 weight % fish gelatin and about 65-75 weight % bovine gelatin.

11. The capsule of claim 8, wherein fish gelatin comprises about 28 weight % and bovine gelatin comprises about 72 weight %.

12. The capsule of claim 1, wherein the at least one gelatin is a combination of a plurality of fish gelatins.

13. The capsule film of claim 1, wherein the capsule is formed from a capsule film having a thickness less than about 0.020 inches.

14. The capsule film of claim 1, wherein the capsule is formed from a capsule film having a thickness less than about 0.015 inches.

* * * * *